(12) United States Patent
Worrell

(10) Patent No.: US 12,178,493 B2
(45) Date of Patent: Dec. 31, 2024

(54) SUPPLYING ELECTRICAL ENERGY TO ELECTROSURGICAL INSTRUMENTS

(71) Applicant: CILAG GMBH INTERNATIONAL, Zug (CH)

(72) Inventor: Barry Christian Worrell, Maineville, OH (US)

(73) Assignee: Cilag GmbH International, Zug (CH)

( * ) Notice: Subject to any disclaimer, the term of this patent is extended or adjusted under 35 U.S.C. 154(b) by 208 days.

(21) Appl. No.: 17/509,555

(22) Filed: Oct. 25, 2021

(65) Prior Publication Data

US 2022/0133388 A1 May 5, 2022

Related U.S. Application Data

(63) Continuation of application No. 15/919,512, filed on Mar. 13, 2018, now Pat. No. 11,160,601.

(51) Int. Cl.
*A61B 18/14* (2006.01)
*A61B 18/12* (2006.01)
(Continued)

(52) U.S. Cl.
CPC ...... *A61B 18/1206* (2013.01); *A61B 18/1445* (2013.01); *A61B 34/30* (2016.02); *A61B 17/00234* (2013.01); *A61B 2017/00477* (2013.01); *A61B 17/29* (2013.01); *A61B 2017/2927* (2013.01); *A61B 17/3201* (2013.01); *A61B 2018/00178* (2013.01); *A61B 2018/00601* (2013.01); *A61B 2018/0063* (2013.01); *A61B 2018/00702* (2013.01);
(Continued)

(58) Field of Classification Search
CPC ............ A61B 18/1442; A61B 18/1445; A61B 18/1482; A61B 18/085; A61B 2018/00178; A61B 2018/00601; A61B 2018/0063; A61B 2018/126; A61B 2018/00607; A61B 2018/00589; A61B 2018/00595; A61B 2018/00202; A61B 2017/2927; A61B 17/29; A61B 34/30; A61B 34/71; A61B 2034/305
USPC .... 606/41, 45, 48–52; 607/98, 99, 101, 115, 607/116
See application file for complete search history.

(56) References Cited

U.S. PATENT DOCUMENTS 6,840,938 B1 * 1/2005 Morley .................. A61B 34/71
901/29
7,524,320 B2 4/2009 Tierney et al.
(Continued)

FOREIGN PATENT DOCUMENTS

CN 102143714 A 8/2011
CN 105025820 A 11/2015
(Continued)

*Primary Examiner* — Thomas A Giuliani

(57) ABSTRACT

An end effector for a surgical tool includes a distal clevis, first and second jaws rotatably mounted to the distal clevis at a first axle, a proximal clevis rotatably coupled to the distal clevis at a second axle, and an electrical conductor extending through and electrically bypassing the proximal clevis and terminating at the distal clevis to supply electrical energy to at least one of the first and second jaws via conduction. A portion of the electrical conductor provides a conductive spring member that allows the electrical conductor to flex as the distal clevis articulates.

2 Claims, 6 Drawing Sheets

(51) Int. Cl.
*A61B 34/30* (2016.01)
*A61B 17/00* (2006.01)
*A61B 17/29* (2006.01)
*A61B 17/3201* (2006.01)
*A61B 18/00* (2006.01)
*A61B 34/35* (2016.01)

(52) U.S. Cl.
CPC ............... *A61B 2018/1226* (2013.01); *A61B 2018/1253* (2013.01); *A61B 2018/126* (2013.01); *A61B 2034/302* (2016.02); *A61B 2034/305* (2016.02); *A61B 34/35* (2016.02)

(56) References Cited

U.S. PATENT DOCUMENTS

| | | | |
|---|---|---|---|
| 7,824,401 B2 * | 11/2010 | Manzo | A61B 34/30 |
| | | | 901/29 |
| 7,879,035 B2 | 2/2011 | Garrison et al. | |
| 8,241,283 B2 | 8/2012 | Guerra et al. | |
| 8,361,072 B2 | 1/2013 | Dumbauld et al. | |
| 8,394,095 B2 | 3/2013 | Garrison et al. | |
| 8,696,667 B2 | 4/2014 | Guerra et al. | |
| 9,138,284 B2 | 9/2015 | Krom et al. | |
| 11,160,601 B2 * | 11/2021 | Worrell | A61B 34/30 |
| 2003/0199869 A1 * | 10/2003 | Johnson | A61B 18/1445 |
| | | | 606/50 |
| 2006/0079884 A1 | 4/2006 | Manzo et al. | |
| 2007/0123855 A1 | 5/2007 | Morley | |
| 2009/0326530 A1 * | 12/2009 | Orban, III | A61B 34/71 |
| | | | 606/51 |
| 2010/0016853 A1 * | 1/2010 | Burbank | A61B 18/1445 |
| | | | 606/48 |
| 2011/0196419 A1 * | 8/2011 | Cooper | A61B 17/29 |
| | | | 606/206 |
| 2015/0025549 A1 | 1/2015 | Kilroy et al. | |
| 2015/0105701 A1 | 4/2015 | Mayer et al. | |
| 2015/0209965 A1 | 7/2015 | Low et al. | |
| 2015/0359587 A1 | 12/2015 | Krom et al. | |
| 2019/0105099 A1 * | 4/2019 | Murrell | A61B 34/74 |

FOREIGN PATENT DOCUMENTS

| | | |
|---|---|---|
| EP | 3466362 A1 | 4/2019 |
| KR | 20110052626 A | 5/2011 |
| WO | 2010009223 A2 | 1/2010 |
| WO | 2011/097095 A1 | 8/2011 |
| WO | 2014134034 A2 | 9/2014 |

* cited by examiner

SUPPLYING ELECTRICAL ENERGY TO ELECTROSURGICAL INSTRUMENTS

CROSS-REFERENCE TO RELATED APPLICATION(S)

This application is a continuation of U.S. Non-Provisional application Ser. No. 15/919,512 filed Mar. 13, 2018, now U.S. Pat. No. 11,160,601, the contents of which is incorporated herein by reference in its entirety for all purposes.

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The trocar also helps facilitate insufflation to elevate the abdominal wall above the organs. The instruments and tools introduced into the abdominal cavity via the trocar can be used to engage and/or treat tissue in a number of ways to achieve a diagnostic or therapeutic effect.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation. The instrument's end effector can be articulated (moved) using a cable driven motion system having one or more drive cables that extend through the wrist joint. A user (e.g., a surgeon) is able to remotely operate an instrument's end effector by grasping and manipulating in space one or more controllers that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations.

Some surgical tools, commonly referred to as electrosurgical instruments, are electrically energized. An electrosurgical instrument has a distally mounted end effector that includes one or more electrodes. When supplied with electrical energy, the end effector electrodes are able to generate heat sufficient to cut, cauterize, and/or seal tissue.

Electrosurgical instruments can be configured for bipolar or monopolar operation. In bipolar operation, current is introduced into and returned from the tissue by active and return electrodes, respectively, of the end effector. Electrical current in bipolar operation is not required to travel long distances through the patient before returning to the return electrode. Consequently, the amount of electrical current required is minimal, which greatly reduces the risk of accidental ablations and/or burns. In addition, the two electrodes are closely spaced and generally within the surgeon's field of view, which further reduces the risk of unintended ablations and burns.

In monopolar operation, current is introduced into the tissue by an active end effector electrode (alternately referred to as a "source electrode") and returned through a return electrode (e.g., a grounding pad) separately located on a patient's body. Monopolar electrosurgical instruments facilitate several surgical functions, such as cutting tissue, coagulating tissue to stop bleeding, or concurrently cutting and coagulating tissue. The surgeon can apply a current whenever the conductive portion of the instrument is in electrical proximity with the patient, permitting the surgeon to operate with monopolar electrosurgical instruments from many different angles.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to electrosurgical instruments having an end effector with a wrist and an electrical conductor that terminates at a distal clevis of the wrist.

Embodiments discussed herein describe electrosurgical instruments that use electrical energy to perform a variety of surgical procedures. End effectors that may be used with the electrosurgical instruments include a distal clevis, first and second jaws rotatably mounted to the distal clevis at a first axle, and a proximal clevis rotatably coupled to the distal clevis at a second axle. An electrical conductor may extend through the proximal clevis and terminates at the distal clevis to supply electrical energy to at least one of the first and second jaws. Accordingly, the electrical conductor may be configured to supply electrical energy directly to the distal clevis and otherwise bypass energizing the proximal clevis.

Figure 1:
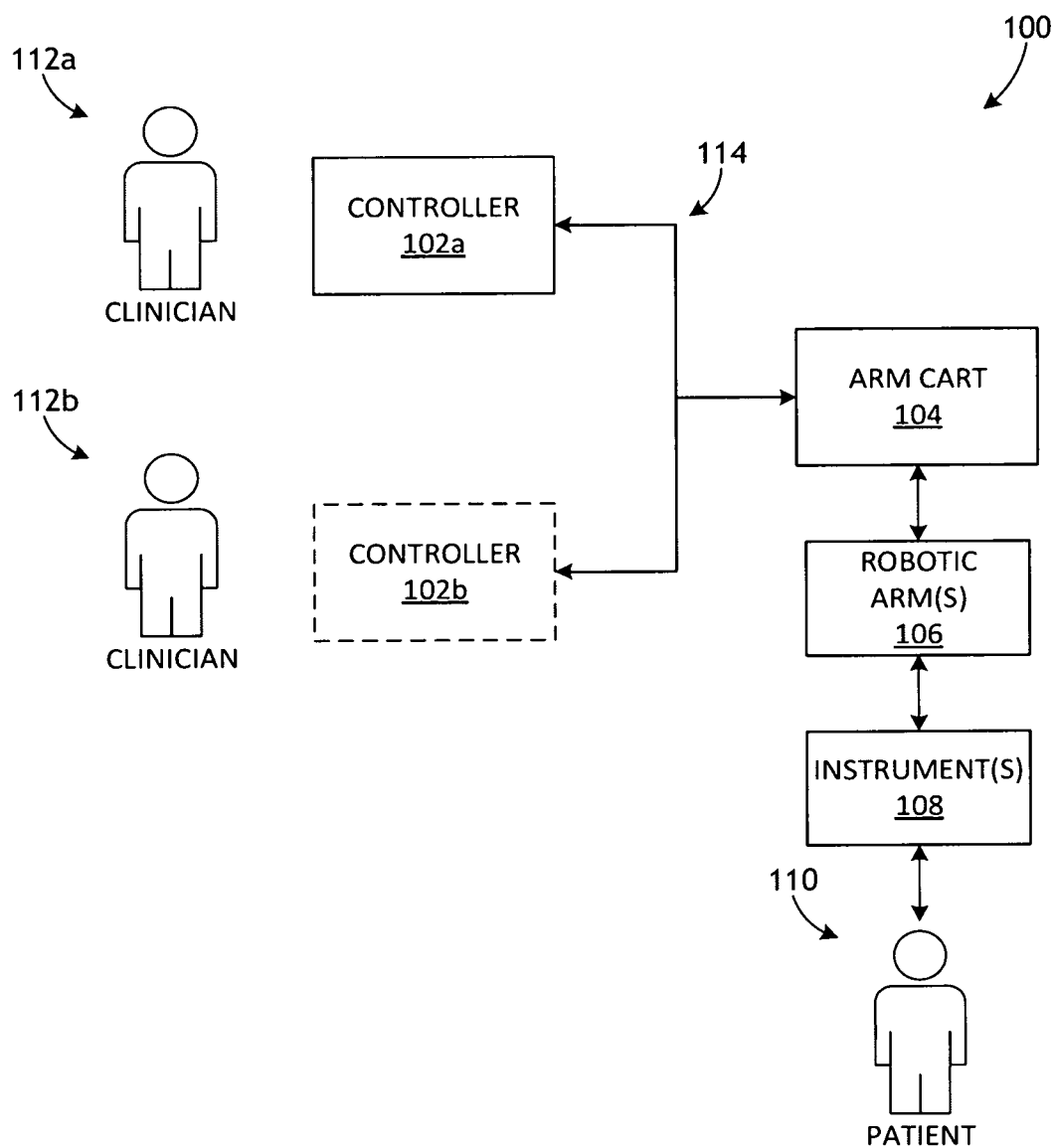
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to a robotic manipulator and, more particularly, to one or more robotic arms 106 or "tool drivers". Each robotic arm 106 may include and otherwise provide a location for mounting one or more surgical tools or instruments 108 for performing various surgical tasks on a patient 110. Operation of the robotic arms 106 and instruments 108 may be directed by a clinician 112a (e.g., a surgeon) from the master controller 102a.

In some embodiments, a second master controller 102b (shown in dashed lines) operated by a second clinician 112b may also direct operation of the robotic arms 106 and instruments 108 in conjunction with the first clinician 112a. In such embodiments, for example, each clinician 102a,b may control different robotic arms 106 or, in some cases, complete control of the robotic arms 106 may be passed between the clinicians 102a,b. In some embodiments, additional arm carts (not shown) having additional robotic arms (not shown) may be utilized during surgery on a patient 110, and these additional robotic arms may be controlled by one or more of the master controllers 102a,b.

The arm cart 104 and the master controllers 102a,b may be in communication with one another via a communications link 114, which may be any type of wired or wireless telecommunications means configured to carry a variety of communication signals (e.g., electrical, optical, infrared, etc.) according to any communications protocol.

The master controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical instrument(s) 108, for example, for opening and closing opposing jaws, applying an electrical potential (current) to an electrode, or the like. The master controllers 102a,b can also include an optional feedback meter viewable by the clinicians 112a,b via a display to provide a visual indication of various surgical instrument metrics, such as the amount of force being applied to the surgical instrument (i.e., a cutting instrument or dynamic clamping member).

Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand the various embodiments and forms of the various embodiments of robotic surgery apparatus, systems, and methods disclosed herein.

Figure 2:
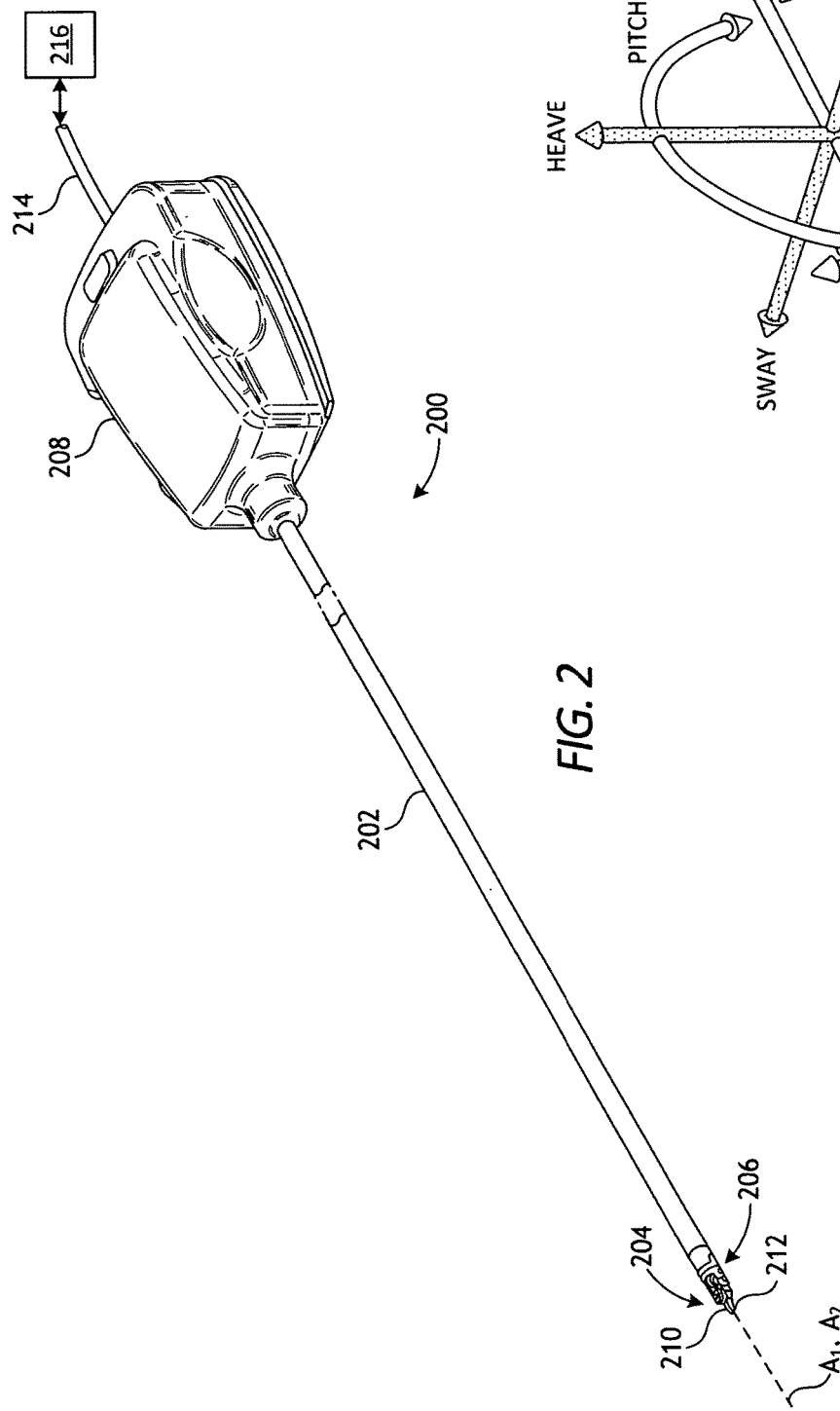
FIG. 2 is an isometric view of an example surgical tool that may incorporate some or all of the principles of the present disclosure.

FIG. 2 is side view of an example surgical tool 200 that may incorporate some or all of the principles of the present disclosure. The surgical tool 200 may be the same as or similar to the surgical instrument(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, the surgical tool 200 may be adapted for use in a manual or hand-operated manner, without departing from the scope of the disclosure.

As illustrated, the surgical tool 200 includes an elongate shaft 202, an end effector 204, a wrist 206 (alternately referred to as a "wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. The housing 208 includes (contains) various mechanisms designed to control operation of various features associated with the end effector 204 (e.g., clamping, firing, rotation, articulation, energy delivery, etc.). In at least some embodiments, the shaft 202, and hence the end effector 204 coupled thereto, is configured to rotate about a longitudinal axis $A_1$ of the shaft 202. In such embodiments, at least one of the mechanisms included (housed) in the housing 208 is configured to control rotational movement of the shaft 202 about the longitudinal axis $A_1$.

The surgical tool 200 can have any of a variety of configurations capable of performing at least one surgical function. For example, the surgical tool 200 may include, but is not limited to, forceps, a grasper, a needle driver, scissors, an electrocautery tool, a stapler, a clip applier, a hook, a spatula, a suction tool, an irrigation tool, an imaging device (e.g., an endoscope or ultrasonic probe), or any combination thereof. In some embodiments, the surgical tool 200 may be configured to apply energy to tissue, such as radio frequency (RF) energy.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can have a variety of sizes, shapes, and configurations. In the illustrated embodiment, the end effector 204 comprises surgical scissors that include opposing jaws 210, 212 (alternately referred to as "blades") configured to move (articulate) between open and closed positions. As will be appreciated, however, the opposing jaws 210, 212 may alternatively form part of other types of end effectors such as, but not limited to, a tissue grasper, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot at the wrist 206 to articulate the end effector 204 between the open and closed positions.

Figure 3:
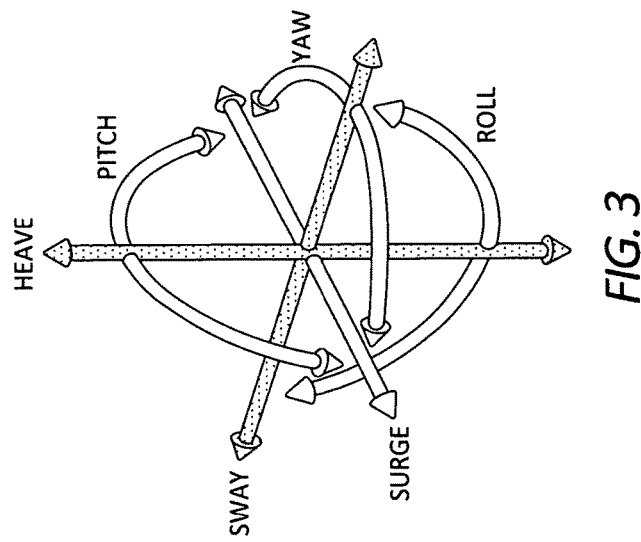
FIG. 3 illustrates potential degrees of freedom in which the wrist of FIG. 1 may be able to articulate (pivot).

FIG. 3 illustrates the potential degrees of freedom in which the wrist 206 may be able to articulate (pivot). The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 204) with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting about an axis, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate movement and articulation of the end effector 204 relative to the shaft 202. Moving (actuating) at least some of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

Still referring to FIG. 2, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries or fuel cells. For purposes of the present description, however, it will be assumed that electrical power is provided to the surgical tool 200 via the power cable 214. In either case, the surgical tool 200 may alternatively be characterized and otherwise referred to herein as an "electrosurgical instrument" capable of providing electrical energy to the end effector 204.

The power cable 214 may place the surgical tool 200 in communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

In applications where the surgical tool 200 is configured for bipolar operation, the power cable 214 will include a supply conductor and a return conductor. Current can be supplied from the generator 216 to an active (or source) electrode located at the end effector 204 via the supply conductor, and current can flow back to the generator 216 via a return conductor located at the end effector 204 via the return conductor. In the case of a bipolar grasper with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 200 is configured for monopolar operation, the generator 216 transmits current through a supply conductor to an active electrode located at the end effector 204, and current is returned (dissipated) through a return electrode (e.g., a grounding pad) separately coupled to a patient's body.

Figure 4:
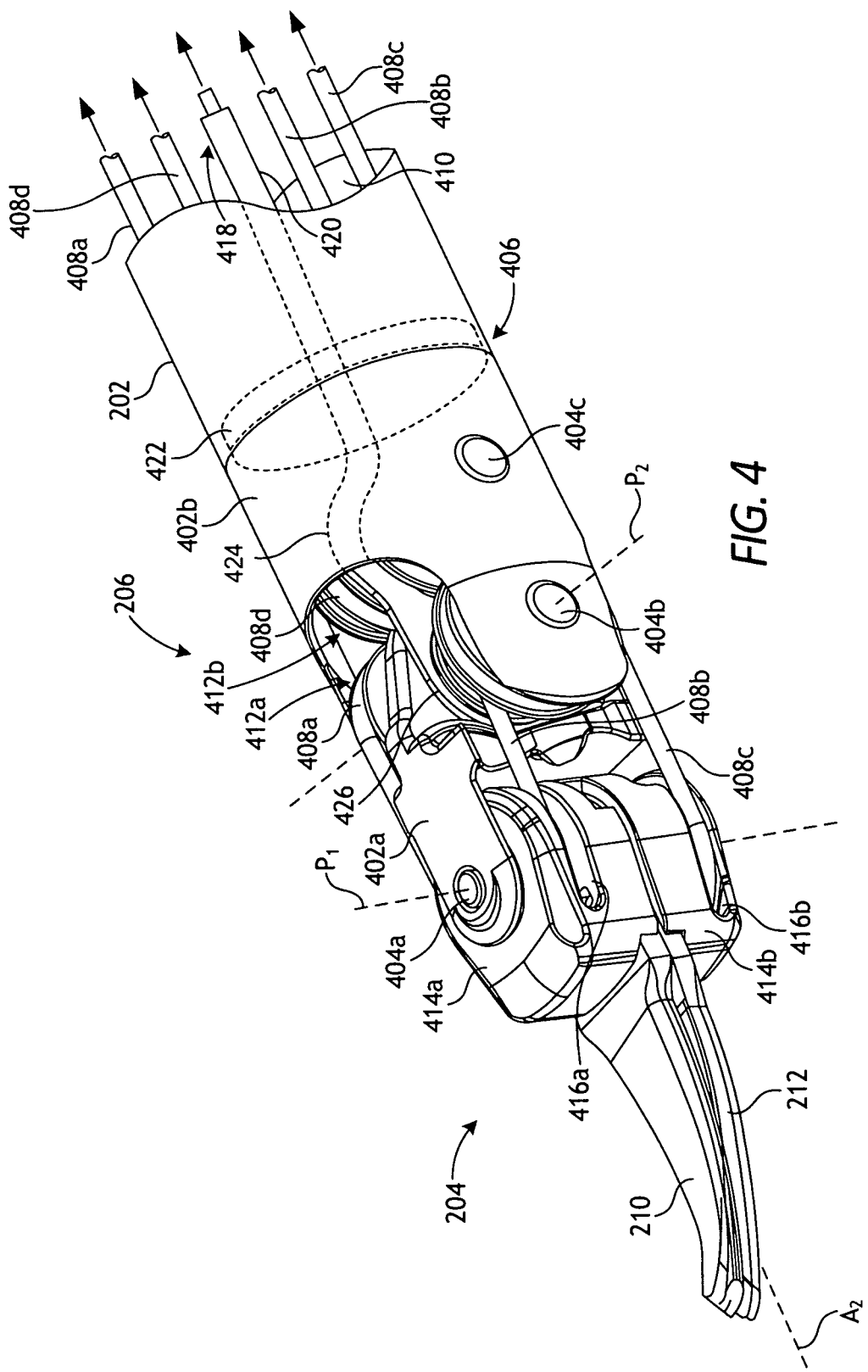
FIG. 4 is an enlarged isometric view of the distal end of the surgical tool of FIG. 1.

FIG. 4 is an enlarged isometric view of the distal end of the surgical tool 200 of FIG. 2. More specifically, FIG. 4 depicts enlarged views of the end effector 204 and the wrist 206, with the end effector 204 in the unarticulated position. The wrist 206 operatively couples the end effector 204 to the shaft 202. In some embodiments, however, a shaft adapter may be directly coupled to the wrist 206 and otherwise interpose the shaft 202 and the wrist 206. Accordingly, in at least one embodiment, the shaft 202 shown in FIG. 4 may be replaced with a shaft adapter. In such embodiments, the shaft adapter may be directly coupled to the wrist 206 at its distal end and directly coupled to the shaft 202 at its proximal end, without departing from the scope of the disclosure. As used herein, the term "operatively couple" refers to a direct or indirect coupling engagement. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202.

To operatively couple the end effector 204 to the shaft 202, the wrist 206 includes a distal clevis 402a and a proximal clevis 402b. The end effector 204 (i.e., the jaws 210, 212) is rotatably mounted to the distal clevis 402a at a first axle 404a, the distal clevis 402a is rotatably mounted to the proximal clevis 402b at a second axle 404b, and the proximal clevis 402b is coupled to a distal end 406 of the shaft 202 (or alternatively a shaft adapter).

The wrist 206 provides a first pivot axis $P_1$ that extends through the first axle 404a and a second pivot axis $P_2$ that extends through the second axle 404b. The first pivot axis $P_1$ is substantially perpendicular (orthogonal) to the longitudinal axis $A_2$ of the end effector 204, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 204, and movement about the second pivot axis $P_2$ provides "pitch" articulation of the end effector 204. In the illustrated embodiment, the jaws 210, 212 are mounted at the first pivot axis $P_1$, thereby allowing the jaws 210, 212 to pivot relative to each other to open and close the end effector 204 or alternatively pivot in tandem to articulate the orientation of the end effector 204.

A plurality of drive cables, shown as drive cables 408a, 408b, 408c, and 408d, extend longitudinally within a lumen 410 defined by the shaft 202 (and/or a shaft adaptor) and pass through the wrist 206 to be operatively coupled to the end effector 204. While four drive cables 408a-d are depicted in FIG. 4, more or less than four drive cables 408a-d may be included, without departing from the scope of the disclosure.

The drive cables 408a-d form part of the cable driven motion system briefly described above, and may be referred to and otherwise characterized as cables, bands, lines, cords, wires, ropes, strings, twisted strings, elongate members, etc. The drive cables 408a-d can be made from a variety of materials including, but not limited to, metal (e.g., tungsten, stainless steel, etc.) or a polymer. Example drive cables are described in U.S. Patent Pub. No. 2015/0209965 entitled "Compact Robotic Wrist," and U.S. Patent Pub. No. 2015/0025549 entitled "Hyperdexterous Surgical System," the contents of which are hereby incorporated by reference. The lumen 410 can be a single lumen, as illustrated, or can alternatively comprise a plurality of independent lumens that each receive one or more of the drive cables 408a-d.

The drive cables 408a-d extend proximally from the end effector 204 to the drive housing 208 (FIG. 2) where they are operatively coupled to various actuation mechanisms or devices housed (contained) therein to facilitate longitudinal movement (translation) of the drive cables 408a-d within the lumen 410. Selective actuation of all or a portion of the drive cables 408a-d causes the end effector 204 (e.g., one or both of the jaws 210, 212) to articulate (pivot) relative to the shaft 202. More specifically, selective actuation causes a corresponding drive cable 408a-d to translate longitudinally within the lumen 410 and thereby cause pivoting movement of the end effector 204. One or more drive cables 408a-d, for example, may translate longitudinally to cause the end effector 204 to articulate (e.g., both of the jaws 210, 212 angled in a same direction), to cause the end effector 204 to open (e.g., one or both of the jaws 210, 212 move away from the other), or to cause the end effector 204 to close (e.g., one or both of the jaws 210, 212 move toward the other).

Moving the drive cables 408a-d can be accomplished in a variety of ways, such as by triggering an associated actuator or mechanism operatively coupled to or housed within the drive housing 208 (FIG. 2). Moving a given drive cable 408a-d constitutes applying tension (i.e., pull force) to the given drive cable 408a-d in a proximal direction, which causes the given drive cable 408a-d to translate and thereby cause the end effector 204 to move (articulate) relative to the shaft 202.

The wrist 206 includes a first plurality of pulleys 412a and a second plurality of pulleys 412b, each configured to interact with and redirect the drive cables 408a-d for engagement with the end effector 204. The first plurality of pulleys 412a is mounted to the proximal clevis 402b at the second axle 404b and the second plurality of pulleys 412b is also mounted to the proximal clevis 402b but at a third axle 404c located proximal to the second axle 404b. The first and second pluralities of pulleys 412a,b cooperatively redirect the drive cables 408a-d through an "S" shaped pathway before the drive cables 408a-d are operatively coupled to the end effector 204.

In at least one embodiment, one pair of drive cables 408a-d is operatively coupled to each jaw 210, 212 and configured to "antagonistically" operate the corresponding jaw 210, 212. In the illustrated embodiment, for example, the first and second drive cables 408a,b are coupled with a connector (not shown) at the first jaw 210, and the third and fourth drive cables 408c,d are coupled with a connector (not shown) at the second jaw 212. Consequently, actuation of the first drive cable 408a pivots the first jaw 210 about the first pivot axis $P_1$ toward the open position, and actuation of the second drive cable 408b pivots the first jaw 210 about the first pivot axis $P_1$ in the opposite direction and toward the closed position. Similarly, actuation of the third drive cable 408c pivots the second jaw 212 about the first pivot axis $P_1$ toward the open position, while actuation of the fourth drive cable 408d pivots the second jaw 212 about the first pivot axis $P_1$ in the opposite direction and toward the closed position.

Accordingly, the drive cables 408a-d may be characterized or otherwise referred to as "antagonistic" cables that cooperatively (yet antagonistically) operate to cause relative or tandem movement of the first and second jaws 210, 212. When the first drive cable 408a is actuated (moved), the second drive cable 408b naturally follows as coupled to the first drive cable 408a, and when the third drive cable 408c is actuated, the fourth drive cable 408d naturally follows as coupled to the third drive cable 408c, and vice versa.

The end effector 204 further includes a first jaw holder 414a and a second jaw holder 414b laterally offset from the first jaw holder 414a. The first jaw holder 414a is mounted to the first axle 404a and configured to receive and seat the first jaw 210 such that movement (rotation) of the first jaw holder 414a about the first pivot axis $P_1$ correspondingly moves (rotates) the first jaw 210. The first jaw holder 414a may also provide and otherwise define a first pulley 416a configured to receive and seat one or more drive cables, such as the first and second drive cables 408a,b to effect such movement (rotation). The second jaw holder 414b is similarly mounted to the first axle 404a and is configured to receive and seat the second jaw 212 such that movement (rotation) of the second jaw holder 414b about the first pivot axis $P_1$ correspondingly moves (rotates) the second jaw 212. The second jaw holder 414b may also provide and otherwise define a second pulley 416b configured to receive and seat one or more drive cables, such as the third and fourth drive cables 408c,d, to effect such movement (rotation).

The term "jaw holder," as used herein, is intended to apply to a variety of types of end effectors having opposing jaws or blades that are movable relative to one another. In the illustrated embodiment, the jaws 210, 212 comprise opposing scissor blades of a surgical scissors end effector. Accordingly, the jaw holders 414a,b may alternately be referred to as "blade holders". In other embodiments, however, the jaws 210, 212 may alternatively comprise opposing jaws used in a grasper end effector, or the like, and the term "jaw holder" similarly applies, without departing from the scope of the disclosure. Moreover, the term "holder" in "jaw holder" may be replaced with "mount," "drive member," or "actuation member."

The surgical tool 200 may also include an electrical conductor 418 that supplies electrical energy to the end effector 204, thereby converting the surgical tool 200 into an "electrosurgical instrument". Similar to the drive cables 408a-d, the electrical conductor 418 may extend longitudinally within the lumen 410. In some embodiments, the electrical conductor 418 and the power cable 214 (FIG. 2) may comprise the same structure. In other embodiments, however, the electrical conductor 418 may be electrically coupled to the power cable 214, such as at the drive housing 208 (FIG. 2). In yet other embodiments, the electrical conductor 418 may extend to the drive housing 208 where it is electrically coupled to an internal power source, such as batteries or fuel cells.

In some embodiments, the electrical conductor 418 may comprise a wire. In other embodiments, however, the electrical conductor 418 may comprise a rigid or semi-rigid shaft, rod, or strip (ribbon) made of a conductive material. In some embodiments, the electrical conductor 418 may be partially covered with an insulative covering 420 made of a non-conductive material. The insulative covering 420, for example, may comprise a plastic applied to the electrical conductor 418 via heat shrinking, but could alternatively be any other non-conductive material.

In operation, the end effector 204 may be configured for monopolar or bipolar operation, without departing from the scope of the disclosure. Electrical energy is transmitted by the electrical conductor 418 to the end effector 204, which acts as an active (or source) electrode. In at least one embodiment, the electrical energy conducted through the electrical conductor 418 may comprise radio frequency ("RF") energy exhibiting a frequency between about 100 kHz and 1 MHz. The RF energy causes ultrasonic agitation or friction, in effect resistive heating, thereby increasing the temperature of target tissue. Accordingly, electrical energy supplied to the end effector 204 is converted to heat and transferred to adjacent tissue to cut, cauterize, and/or coagulate the tissue (dependent upon the localized heating of the tissue), and thus may be particularly useful for sealing blood vessels or diffusing bleeding.

Conventional electrosurgical instruments with an articulable wrist will commonly include an electrical conductor that terminates at the proximal clevis, and the structural interconnection between the distal and proximal clevises provides the required electrical energy to energize the end effector for operation. Terminating the electrical conductor at the proximal clevis allows the wrist to articulate without being obstructed by the electrical conductor. According to embodiments of the present disclosure, however, the electrical conductor 418 may extend through and otherwise bypass the proximal clevis 402b to terminate at the distal clevis 402a. Consequently, the electrical conductor 418 may deliver electrical energy to the distal clevis 402a, which may be transmitted to one or both of the jaws 210, 212 via conduction.

As illustrated, a seal 422 (shown in dashed lines) may be arranged at the interface between the proximal clevis 402b and the shaft 102 (or alternatively a shaft adapter). The seal 422 may be configured to substantially isolate the interior of the shaft 102 from the end effector 204 by preventing the migration of contaminants and fluid therethrough in either direction. As illustrated in dashed lines, the electrical conductor 418 may extend through the seal 422 and the proximal clevis 402b before terminating at the proximal end of the distal clevis 402a.

In at least one embodiment, the electrical conductor 418 may provide or otherwise define an arcuate section 424 that allows the electrical conductor 418 to pass through the proximal clevis 402b without coming into contact with (engaging) some or all of the proximal clevis 402b, the second axle 404b, or the second plurality of pulleys 412b. In other embodiments, the arcuate section 424 may be omitted and the electrical conductor 418 may nonetheless be arranged to pass through the proximal clevis 402b without engaging these structural components.

As illustrated, the electrical conductor 418 may terminate at a conductor adapter 426. The conductor adapter 426 may be made of a conductive material, such as a conductive metal, and configured to transmit (conduct) electrical energy from the electrical conductor 418 to the distal clevis 402a. In the illustrated embodiment, the conductor adaptor 426 is assembled on the second axle 404b and interposes the first plurality of pulleys 412a and a proximal end of the distal clevis 402a. The first plurality of pulleys 412a may be made of a conductive material and may be suitably insulated from conducting electrical energy to the proximal clevis 402b. In other embodiments, however, the first plurality of pulleys 412a may be made of any electrically insulating or non-conductive material to insulate the distal end of the proximal pulley 402b from the conductor adaptor 426 and the electrical energy supplied to the distal clevis 402a. Suitable non-conductive materials include, but are not limited to, a ceramic (e.g., zirconia, alumina, aluminum nitride, a silicate, silicon nitride, etc.), high temperature and high strength plastics, a thermoplastic or thermosetting polymer (e.g., polyether ether ketone, ULTEM™, VESPEL®, a polyphenylsulfone, a polysulfone, RADEL®, a polyamide-imide, a polyimide, an epoxy, etc.), a composite material (e.g., fiberglass), hard rubber (e.g., ebonite), a metal with an insulative coating, or any combination thereof.

The conductor adapter 426 may contact and otherwise be in electrical engagement (communication) with the distal clevis 402a, which transmits (conducts) the electrical energy supplied by the electrical conductor 418 to at least one of the jaws 210, 212 to energize one or both of the jaws 210, 212 for operation. In some embodiments, for example, the electrical energy is conducted to the jaws 210, 212 through one or both of the first axle 404a and the jaw holders 414a,b, which may be made of a conductive material. In other embodiments, however, the jaw holders 414a,b may be made of a non-conductive material and the electrical energy may alternatively be conducted to one or both of the jaws 210, 212 through the first axle 404a.

Figure 5:
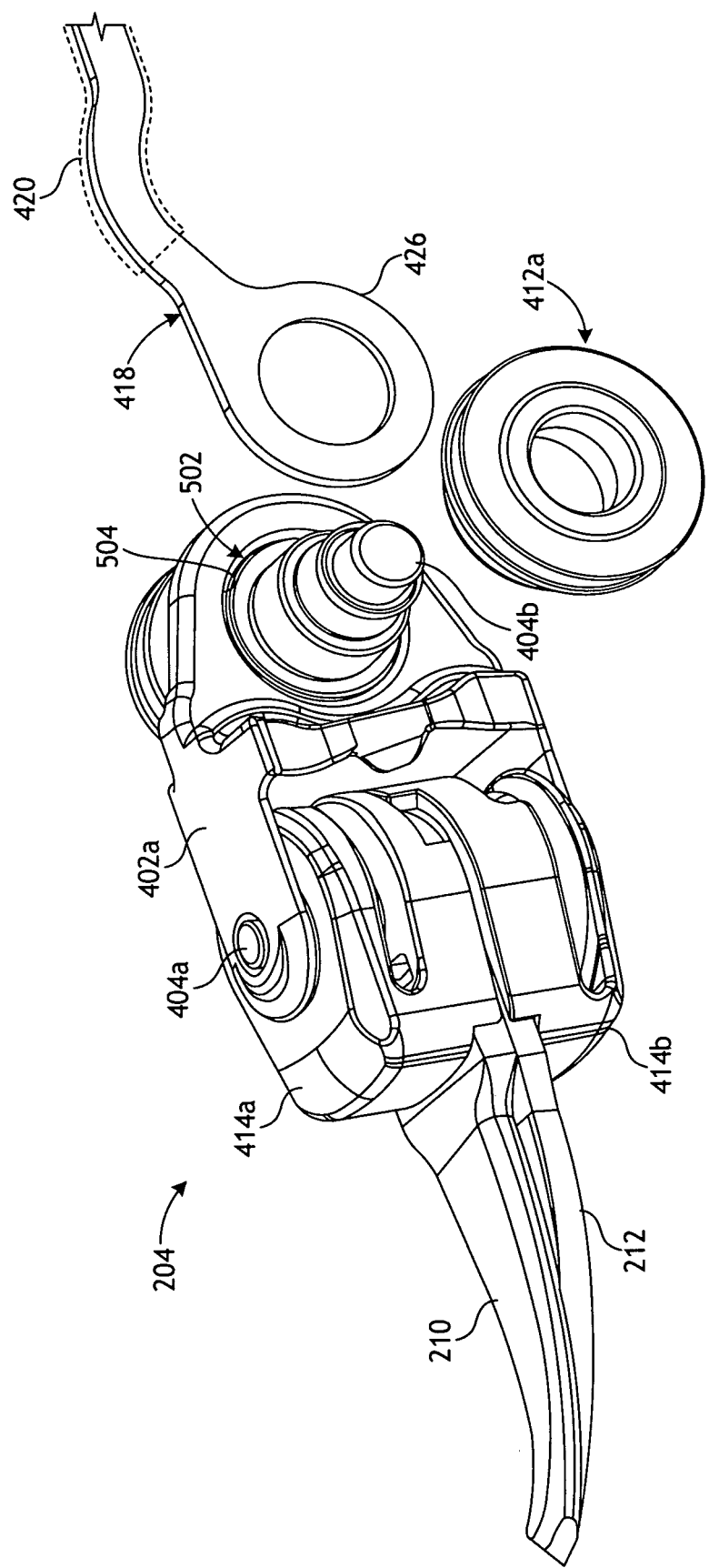
FIG. 5 is an enlarged, partially exploded view of the end effector of FIG. 4.

FIG. 5 is an enlarged, partially exploded view of the end effector 204, according to one or more embodiments. More specifically, FIG. 5 shows the end effector 204, including the jaws 210, 212 and the corresponding jaw holders 414a,b, mounted to the distal clevis 402a at the first axle 404a. FIG. 5 also shows the electrical conductor 418 and a portion of the first plurality of pulleys 412a exploded or otherwise removed from the second axle 404b.

In the illustrated embodiment, the insulative covering 420 (shown in dashed lines) extends to and terminates adjacent the conductor adapter 426. In such embodiments, the insulative covering 420 may prove advantageous in preventing electrical discharge or communication between the electrical conductor 418 and the proximal clevis 402b (FIG. 4), the second axle 404b (FIG. 4), or the second plurality of pulleys 412b (FIG. 4). In other embodiments, however, the insulative covering 420 may terminate proximal to the proximal clevis 402b and nonetheless be arranged and/or designed to circumvent the proximal clevis 402b, the second axle 404b, and the second plurality of pulleys 412b so as to not inadvertently conduct electrical energy thereto.

As illustrated, the distal clevis 402a may include a bushing 502 that may be seated and otherwise received within an aperture 504 defined in the proximal end of the distal clevis 402a. In some embodiments, the bushing 502 may be made of any of the non-conductive materials mentioned herein, but may alternatively be made of a conductive material and electrical energy may be transmitted to at least one of the jaws 210, 212 via at least a portion of the bushing 502. The bushing 502 may be configured to receive the second axle 404b such that the second axle 404b is able to rotate relative to the bushing 502 during articulation of the end effector 204.

The first plurality of pulleys 412a and the conductor adapter 426 may be mounted to the bushing 502 and may be able to rotate relative to the bushing 502 during articulation of the end effector 204. Accordingly, the conductor adapter 426 may be able to slidingly engage and otherwise ride on the bushing 502 during operation. Consequently, and in contrast to prior electrosurgical instrument, the conductor adapter 426 does not terminate in a solder point or a crimp, but is instead able to "float" on the bushing 502 while providing electrical energy to the distal clevis 402a. In the illustrated embodiment, the bushing 502 provides and otherwise defines varying diameters configured to receive and seat the first plurality of pulleys 412a and the conductor adapter 426, but may alternatively comprise a constant diameter, without departing from the scope of the disclosure.

The conductor adapter 426 encompasses or otherwise comprises the distal end of the electrical conductor 418 and can assume any shape or design capable of facilitating electrical communication between the electrical conductor 418 and the distal clevis 402a. In the illustrated embodiment, for example, the conductor adapter 426 comprises a stamped fisheye connector that defines or provides a continuous annular ring. The conductor adapter 426 may be extended about the bushing 502 to allow the electrical conductor 418 to transmit electrical energy to the distal clevis 402a. In other embodiments, however, the conductor adapter 426 may alternatively comprise a discontinuous annular ring. In yet other embodiments, the conductor adapter 426 may alternatively terminate at a bent portion arranged to be in constant engagement with the bushing 502, without departing from the scope of the disclosure.

Figure 6:
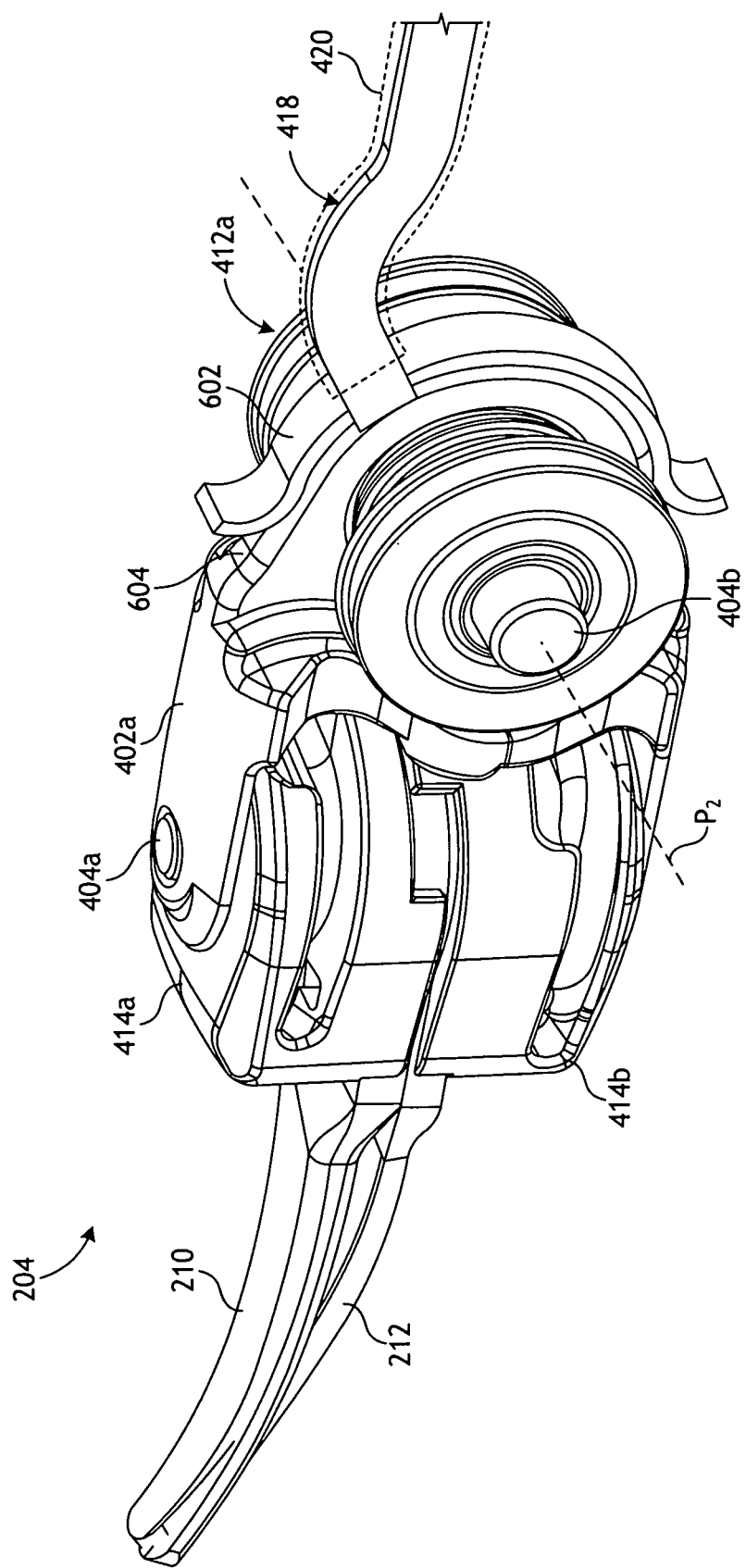
FIG. 6 is an enlarged isometric view of another embodiment of the end effector of FIG. 4.

FIG. 6 is an enlarged isometric view of another embodiment of the end effector 204, according to one or more embodiments. Similar to FIG. 5, FIG. 6 shows the end effector 204, including the jaws 210, 212 and the corresponding jaw holders 414a,b, mounted to the distal clevis 402a at the first axle 404a. Moreover, the first plurality of pulleys 412a is mounted to the second axle 404b for relative rotation. In addition, the electrical conductor 418 extends to and terminates at or near the proximal end of the distal clevis 402a and the insulative covering 420 (shown in dashed lines) may extend along some or all of the length of the electrical conductor 418.

Unlike the embodiment of FIG. 5, however, the electrical conductor 418 terminates in a conductor adapter 602 that is dissimilar to the conductor adapter 426 of FIGS. 4 and 5. More specifically, the conductor adapter 602 may comprise an arcuate member or "saddle" arranged to engage a corresponding arcuate surface 604 of the distal clevis 402a. In the illustrated embodiment, the arcuate surface 604 is defined at the proximal end of the distal clevis 402a, but may alternatively be provided at any other location, without departing from the scope of the disclosure. The conductor adapter 602 may be made of a conductive material, such as a conductive metal (e.g., spring steel, beryllium copper, etc.), and configured to transmit (conduct) electrical energy from the electrical conductor 418 to the distal clevis 402a. In example operation, the distal clevis 402a may articulate about the second pivot axis $P_2$ of the second axle 404b and the conductor adapter 602 may maintain engagement with the arcuate surface 604 during such movement.

Figure 7:
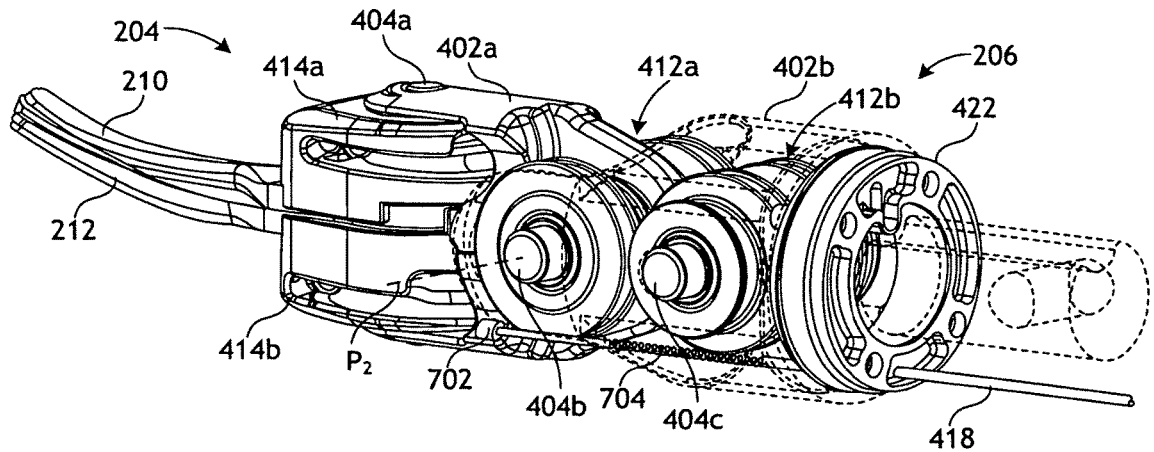
FIG. 7 is an enlarged isometric view of another embodiment of the end effector and the wrist joint of FIG. 4.

FIG. 7 is an enlarged isometric view of another embodiment of the end effector 204 and the wrist joint 206, according to one or more additional embodiments. In the illustrated embodiment, the end effector 204, including the jaws 210, 212 and the corresponding jaw holders 414a,b, is mounted to the distal clevis 402a at the first axle 404a, and the proximal clevis 402b is shown in phantom (dashed lines). Moreover, the first and second pluralities of pulleys 412a,b are mounted to the second and third axles 404b,c, respectively, as generally described above.

In the illustrated embodiment, the electrical conductor 418 extends through the seal 422 and terminates at the distal clevis 402a with a conductor adapter 702. The conductor adapter 702 effectively couples the electrical conductor 418 to the distal clevis 402a such that electrical energy transmitted (conveyed) through the electrical conductor 418 is correspondingly transmitted (conveyed) to the distal clevis 402a during operation. The conductor adapter 702 may comprise, for example, a type of connector such as, but not limited to, a crimp, a solder, a weld, or any combination thereof. In some embodiments, the electrical conductor 418 may include an insulative covering (not shown) that covers some or all of the electrical conductor 418 so that the electrical conductor 418 does not inadvertently conduct electrical energy to the proximal clevis 402b, the second axle 404b, or the second plurality of pulleys 412b.

In some embodiments, at least a portion of the electrical conductor 418 may include or otherwise define a conductive spring member 704. The conductive spring member 704 may comprise a flexible or elastic section of the electrical conductor 418 that allows the end effector 204 to articulate about the second pivot axis $P_2$ of the second axle 404b without losing electrical conductivity through the electrical conductor 418 to the distal clevis 402a. In some embodiments, the conductive spring member 704 may comprise a tightly wound coil of a conductive material, such as Nitinol wire or the like. In other embodiments, the conductive spring member 704 may comprise a flexible, but flat ribbon made of a conductive material. During operation, the conductive spring member 704 may be configured to flex or bend to allow the distal clevis 402a to articulate while still supplying electrical energy thereto.

Figure 8A:
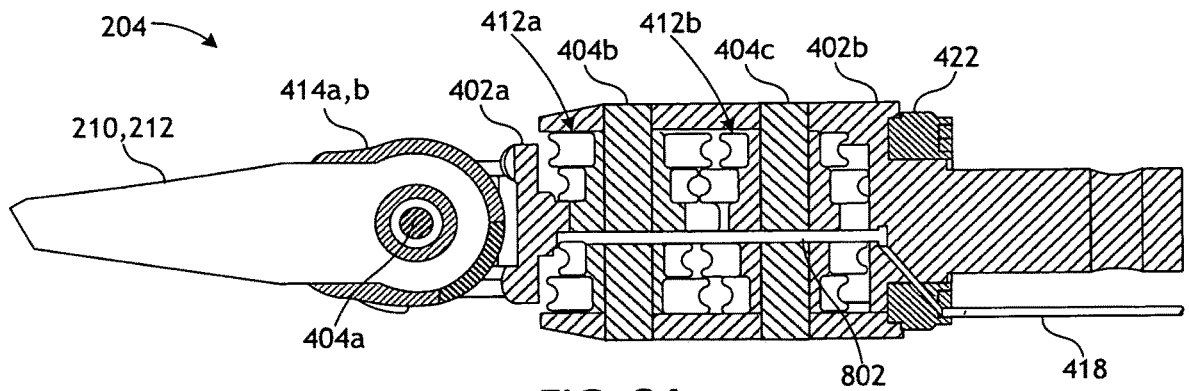
FIG. 8A is an enlarged cross-sectional view of another embodiment of the end effector and the wrist joint of FIG. 4

FIG. 8A is an enlarged cross-sectional view of another embodiment of the end effector 204 and the wrist joint 206, according to one or more embodiments. In the illustrated embodiment, the end effector 204, including the jaws 210, 212 and the corresponding jaw holders 414a,b, is mounted to the distal clevis 402a at the first axle 404a. Moreover, the first and second pluralities of pulleys 412a,b are mounted to the second and third axles 404b,c respectively, which are mounted to the proximal clevis 402b.

In the illustrated embodiment, the electrical conductor 418 extends through the seal 422 and is coupled to a flex circuit 802 that extends through the proximal clevis 402b and terminates at the distal clevis 402a. The flex circuit 802 effectively couples the electrical conductor 418 to the distal clevis 402a such that electrical energy transmitted (conveyed) through the electrical conductor 418 is correspondingly transmitted (conveyed) to the distal clevis 402a during operation. The flex circuit 802 may comprise, for example, a polyimide flexible circuit, but may alternatively be made of polyether ether ketone (PEEK), without departing from the scope of the disclosure.

Figure 8B:
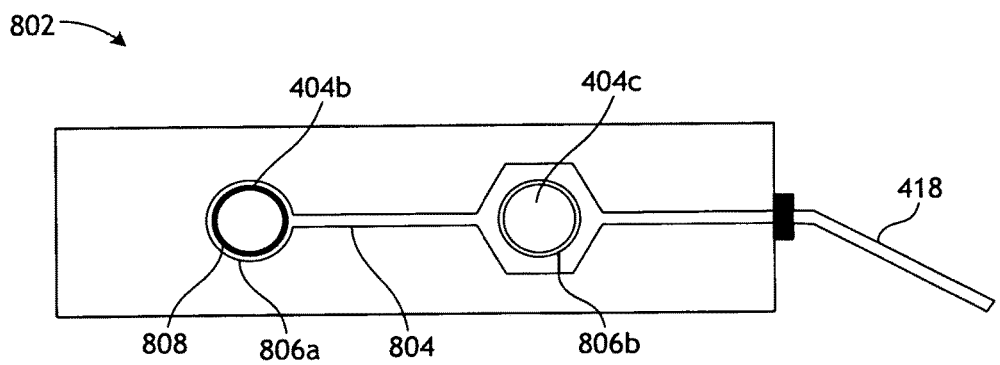
FIG. 8B is a schematic diagram of an example embodiment of the flex circuit of FIG. 8A.

FIG. 8B is a schematic diagram of an example embodiment of the flex circuit 802 of FIG. 8A, according to one or more embodiments of the present disclosure. As illustrated, the flex circuit 802 comprises a substantially flat film with a printed circuit 804 embedded therein. The printed circuit 804 extends from and is communicably coupled to the electrical conductor 418 to convey electrical energy to the distal clevis 402*a* (FIG. 8A).

The flex circuit 802 may include a first aperture 806*a* configured to accommodate the second axle 404*b* and a second aperture 806*b* configured to accommodate the third axle 404*c*. At the first aperture 806*a*, the flex circuit 802 may include an annular conductive pad 808 that places the printed circuit 804 into communication with the distal clevis 402*a* (FIG. 8A). The conductive pad 808 may be made of silver, gold, or another conductive metal that forms an annular ring. Trapping the flex circuit 804 between the bushing 502 (FIG. 5) and the first plurality of pulleys 412*a* (FIG. 8A) provides the electrical conduction path. Accordingly, the conductive pad 808 transfers the energy to the distal clevis 402*a*, which is able to convey the electrical energy to one or both of the jaws 210, 212.

Embodiments disclosed herein include:

A. An end effector that includes a distal clevis, first and second jaws rotatably mounted to the distal clevis at a first axle, a proximal clevis rotatably coupled to the distal clevis at a second axle, and an electrical conductor extending through the proximal clevis and terminating at the distal clevis to supply electrical energy to at least one of the first and second jaws.

B. A surgical tool that includes a drive housing, an elongate shaft that extends from the drive housing, an end effector arranged at a distal end of the elongate shaft and including first and second jaws, a wrist that interposes the end effector and the elongate shaft and includes a distal clevis that rotatably mounts the first and second jaws at a first axle, and a proximal clevis operatively coupled to the elongate shaft and coupled to the distal clevis at a second axle, and an electrical conductor that extends from the drive housing and through the proximal clevis, the electrical conductor terminating at the distal clevis to supply electrical energy to at least one of the first and second jaws.

C. A method of operating a surgical tool that includes positioning the surgical tool adjacent a patient for operation, the surgical tool including a drive housing, an elongate shaft that extends from the drive housing, an end effector arranged at a distal end of the elongate shaft and including first and second jaws, a wrist that interposes the end effector and the elongate shaft and includes a distal clevis that rotatably mounts the first and second jaws at a first axle, and a proximal clevis operatively coupled to the elongate shaft and coupled to the distal clevis at a second axle, and an electrical conductor extending from the drive housing through the proximal clevis and terminating at the distal clevis. The method further including supplying electrical energy to the distal clevis via the electrical conductor and thereby energizing at least one of the first and second jaws.

Each of embodiments A, B, and C may have one or more of the following additional elements in any combination: Element 1: wherein the electrical conductor is selected from the group consisting of a wire, a shaft, a rod, or a strip made of a conductive material. Element 2: further comprising an insulative covering partially covering the electrical conductor. Element 3: wherein the electrical conductor passes through the proximal clevis without coming into contact with the proximal clevis. Element 4: further comprising a conductor adapter arranged at a distal end of the electrical conductor to place the electrical conductor in electrical communication with the distal clevis. Element 5: wherein the conductor adaptor is assembled on the second axle. Element 6: wherein the second axle extends through a bushing seated within an aperture defined in a proximal end of the distal clevis, and wherein the conductor adapter is mounted to the bushing. Element 7: wherein the bushing is made of a non-conductive material selected from the group consisting of a ceramic, a plastic, a thermoplastic or thermosetting polymer, a composite material, hard rubber, a metal with an insulative coating, and any combination thereof. Element 8: wherein the conductor adapter comprises a continuous annular ring. Element 9: wherein the conductor adapter comprises an arcuate member arranged to engage a corresponding arcuate surface of the distal clevis. Element 10: wherein a portion of the electrical conductor defines a conductive spring member.

Element 11: wherein the end effector is configured for monopolar or bipolar operation. Element 12: further comprising a seal arranged at a proximal end of the proximal clevis, wherein the electrical conductor extends through the seal. Element 13: wherein a shaft adapter interposes the wrist and the elongate shaft. Element 14: further comprising a conductor adapter arranged at a distal end of the electrical conductor to place the electrical conductor in electrical communication with the distal clevis. Element 15: wherein the conductor adaptor is assembled on the second axle. Element 16: wherein the conductor adapter comprises an arcuate member arranged to engage a corresponding arcuate surface of the distal clevis.

Element 17: wherein a conductor adapter is arranged at a distal end of the electrical conductor, the method further comprising placing the electrical conductor in electrical communication with the distal clevis with the conductor adapter, and articulating the wrist while maintaining electrical communication with the distal clevis with the conductor adapter.

By way of non-limiting example, exemplary combinations applicable to A, B, and C include: Element 1 with Element 2; Element 4 with Element 5; Element 5 with Element 6; Element 6 with Element 7; Element 4 with Element 8; Element 4 with Element 9; Element 4 with Element 10; Element 14 with Element 15; and Element 14 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An end effector, comprising:
 a distal clevis;
 a first and second jaws rotatably mounted to the distal clevis at a first axle;
 a proximal clevis rotatably coupled to the distal clevis at a second axle;
 and a conductive wire connected to an elongated circuit board that extends distally from the conductive wire through and electrically bypasses the proximal clevis;
 the elongated circuit board comprising a first aperture to accommodate the second axle, a second aperture to accommodate a third axle proximal to the second axle, a printed circuit extending from the conductive wire, around the second aperture to an annular conductive pad arranged at the first aperture;
 wherein the annular conductive pad places the elongated circuit board into electrical communication with the first and second jaw via the distal clevis.

2. The end effector of claim 1, wherein the elongated circuit board comprises a substantially flat film.

* * * * *